_US005438147A_

United States Patent [19]

Jaekel et al.

[11] Patent Number: 5,438,147
[45] Date of Patent: Aug. 1, 1995

[54] IMIDOCARBOXYLIC ACID ACTIVATORS AND SULFIMIDOCARBOXYLIC ACID ACTIVATORS, PROCESSES FOR THEIR PREPARATION AND THEIR USE

[75] Inventors: Frank Jaekel; Gerd Reinhardt, both of Kelkheim; Wolf-Dieter Möller, Hofheim am Taunus, all of Germany

[73] Assignee: Hoechst AG, Frankfurt, Germany

[21] Appl. No.: 876,517

[22] Filed: Apr. 30, 1992

[30] Foreign Application Priority Data

May 4, 1991 [DE] Germany .......... 41 14 583.6

[51] Int. Cl.⁶ .................................... C07D 209/48
[52] U.S. Cl. .................... 548/210; 548/452; 548/473; 548/465; 548/470
[58] Field of Search .......... 548/473, 210, 452, 465, 548/470

[56] References Cited

U.S. PATENT DOCUMENTS

| | | | |
|---|---|---|---|
| 4,248,928 | 2/1981 | Spadini et al. | 428/286 |
| 4,483,781 | 11/1984 | Hartman | 252/174 |
| 4,587,054 | 5/1986 | Hardy et al. | 260/410.5 |
| 4,671,891 | 6/1987 | Hartman | 252/186.42 |
| 4,704,236 | 11/1987 | Sankey et al. | 260/402 |
| 4,735,740 | 4/1988 | Zielske | 252/95 |
| 4,980,482 | 12/1990 | Frazier | 548/520 |
| 5,061,807 | 10/1991 | Gethöffer et al. | 548/473 |
| 5,091,106 | 2/1992 | Jacobs et al. | 252/186 |
| 5,153,189 | 10/1992 | Rupp et al. | 548/210 |

FOREIGN PATENT DOCUMENTS 1211464 9/1986 Canada .
1249300 1/1989 Canada .

OTHER PUBLICATIONS

Kukalenko, S. S. et al., Chem. Abs. 79:91886p (1973).

Primary Examiner—Nicholas Rizzo
Attorney, Agent, or Firm—Connolly and Hutz

[57] ABSTRACT

A persalt activator or salt thereof which is derived from an imidocarboyxlic acid or sulimidocarboxylic acid of the formula I:

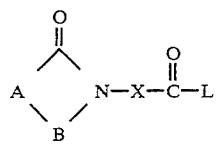

in which A is a group of the formula

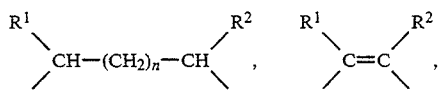

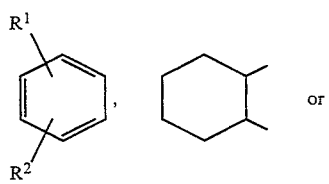

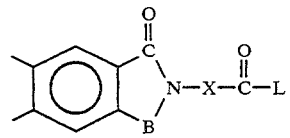

n is the number 0, 1 or 2,
$R^1$ is hydrogen, chlorine, bromine, $C_1$–$C_{20}$-alkyl, $C_2$–$C_{20}$-alkenyl, aryl, or alkylaryl,
$R^2$ is hydrogen, chlorine, bromine or a group of the formula —$SO_3M$, —$CO_2M$ or —$OSO_3M$,
X is $C_1$–$C_{19}$-alkylene or arylene,
B is a group of the formula C═O or $SO_2$, and
L is a leaving group.

6 Claims, No Drawings

IMIDOCARBOXYLIC ACID ACTIVATORS AND SULFIMIDOCARBOXYLIC ACID ACTIVATORS, PROCESSES FOR THEIR PREPARATION AND THEIR USE

The present invention relates to persalt activators and salts thereof which are derived from imidocarboxylic acids and sulfimidocarboxylic acids.

The present invention also relates to a process for the preparation of these persalt activators and salts thereof and their use.

Inorganic persalts have been known for a long time as bleaching additives in detergents. Compounds which liberate hydrogen peroxide in aqueous solution are called inorganic persalts. Customary inorganic persalts include sodium perborate monohydrate, sodium perborate tetrahydrate, sodium percarbonate, sodium peroxomonophosphate, urea peroxohydrate, sodium peroxide and mixtures thereof. However, since they display their optimum bleaching power only at temperatures above 60° C., a number of organic compounds have been described for their activation, these reacting with hydrogen peroxide during the washing process to liberate a peroxycarboxylic acid which already has a bleaching action at 40° to 60° C. Compounds having such a mode of action are called persalt activators or perborate activators.

A review of numerous known persalt activators, such as N-acyl compounds (tetraacetylethylenediamine, tetraacetylmethylenediamine and tetraacetylglycoluril) or activated esters (pentaacetylglucose, sodium acetoxybenzenesulfonate and sodium benzoyloxybenzenesulfonate) is given, for example, in U.S. Pat. No. 4,248,928.

In addition, a number of organic peroxycarboxylic acids have recently been described as bleaching systems for detergents. In addition to already commercially obtainable peroxycarboxylic acids, such as dodecanediperoxycarboxylic acid (EP-A-127 782) and monoperoxyphthalic acid (EP-A-27 693), amidoperoxycarboxylic acids (EP-A-170 386) and imidoperoxycarboxylic acids (EP-A-325 288, EP-A-349 940, EP-A-366 041 and the not yet published German patent application having the application No. P 4 036 647.2) are described. However, when peroxycarboxylic acids are used in commercial bleaching agents, various problems result. Because of the thermal instability of such percompounds, bleaching agents containing peroxycarboxylic acids tend to lose their active oxygen during storage, and a safety problem arises because of their exothermic decomposition reaction. Although these difficulties can be controlled to a certain degree by addition of desensitizing agents (EP-A-376 360, EP-A-105 689, DE-A-2 737 865) and/or an expensive granulating technique (EP-A-396 341, EP-A-256 443, EP-A-272 402 or EP-A-200 163), it has so far not been possible to eliminate the problems completely. Although long-chain peroxycarboxylic acids are distinguished by a better stability, they have the disadvantage that they are almost entirely water-insoluble and are therefore not very suitable for detergent formulations.

For these reasons, there continues to be an urgent need for efficient, storage-stable and readily water-soluble bleaching agents based on persalt activators which liberate the bleaching-active peroxycarboxylic acid only in the wash liquor in combination with an inorganic persalt.

Surprisingly, it has now been found that the persalt activators described below and salts thereof, which are derived from imidocarboxylic acids and sulfimidocarboxylic acids, have a considerably higher storage stability and water-solubility than the previously known persalt activators, and moreover have an excellent bleaching power.

The present invention relates to persalt activators and salts thereof, which are derived from imidocarboxylic acids and sulfimidocarboxylic acids, i.e. from imidocarboxylic acids containing a sulfone group, of the general formula I:

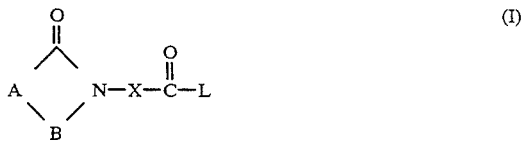

in which A is a group of the formula

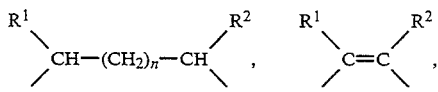

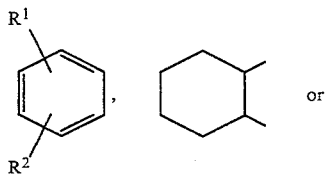

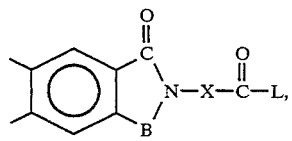

n is the number 0, 1 or 2, $R^1$ is hydrogen, chlorine, bromine, $C_1$–$C_{20}$-alkyl, $C_2$–$C_{20}$-alkenyl, aryl, preferably phenyl, or alkylaryl, preferably $C_1$–$C_4$-alkylphenyl, $R^2$ is hydrogen, chlorine, bromine or a group of the formula —$SO_3M$, —$CO_2M$ or —$OSO_3M$, X is $C_1$–$C_{19}$-alkylene or arylene, preferably phenylene, B is a group of the formula C=O or $SO_2$, L is a leaving group of the formula

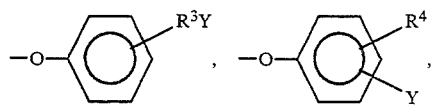

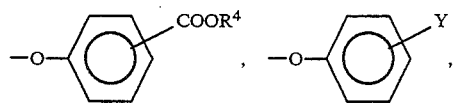

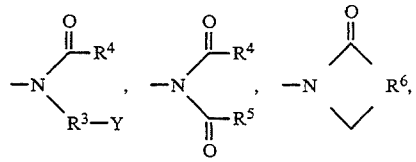

-continued

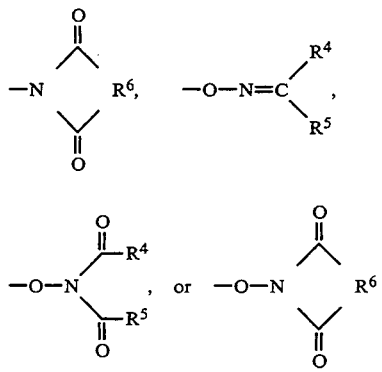

or a sugar residue,
$R^3$ is $C_1$-$C_{19}$-alkylene,
$R^4$ and $R^5$ are $C_1$-$C_{20}$-alkyl,
$R^6$ is $C_1$-$C_{19}$-alkylene or $C_2$-$C_{20}$-alkenylene,
is hydrogen, chlorine, bromine or a group of the formula —$SO_3M$, —$CO_2M$, —$OSO_3M$, —$CONH_2$, —$N(R^7)_3Z$ or —$P(R^7)_4Z$,
$R^7$ is $C_1$-$C_{30}$-alkyl,
Z is fluoride, chloride, bromide or iodide and
M is hydrogen, an alkali metal or ammonium ion or the equivalent of an alkaline earth metal ion.

Preferred persalt activators and salts thereof are those which are derived from imidocarboxylic acids and sulfimidocarboxylic acids of the above formula I in which A is a group of the formula —HC=CH—,

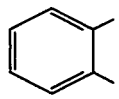

—$CH_2$—$(CH_2)_n$—$CH_2$—,

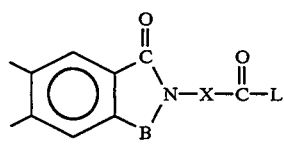

or —$CH_2$—$CHR^1$—,
n is the number 0 or 1,
$R^1$ is $C_1$-$C_{20}$-alkyl or $C_2$-$C_{20}$-alkenyl,
X is $C_4$-$C_8$-alkylene,
B is a group of the formula C=O or $SO_2$,
L is a leaving group of the formula

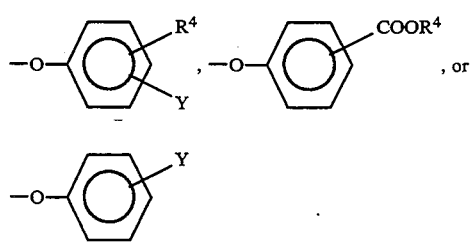

$R^4$ is $C_1$-$C_{20}$-alkyl,

Y is hydrogen or a group of the formula —$SO_3M$, $CO_2M$, $CO_2M$, $CONH_2$, —$OSO_3M$, —$N(R^7)_3Z$ or —$P(R^7)_4Z$,
$R^7$ is $C_1$-$C_4$-alkyl, particularly preferably methyl,
Z is chloride and
M is hydrogen, an alkali metal or ammonium ion or the equivalent of an alkaline earth metal ion.

ω-Phthalimidoalkanoyloxybenzenecarboxylic acids and salts thereof, ω-phthalimidoalkanoyloxybenzenesulfonic acids and salts thereof, ω-2-alkylsuccinimidoalkanoyloxybenzenecarboxylic acids and salts thereof, ω-2-alkylsuccinimidoalkanoyloxybenzenesulfonic acids and salts thereof, ω-[1,1,3-trioxo-3H-λ$^6$-benz[α]isothiazol-2-yl]-alkanoyloxybenzenecarboxylic acids and salts thereof and ω-[1,1,3-trioxo-3H-λ$^6$-benz[α]isothiazol-2-yl ]-alkanoyloxybenzenesulfonic acids and salts thereof are particularly preferred.

The invention also relates to a process for the preparation of the persalt activators and salts thereof according to the invention, and to their use as bleaching, oxidizing and disinfecting agents.

The persalt activators and salts thereof of the formula I which are derived from imidocarboxylic acids are prepared by the following steps:
  -a- Synthesis of the imidocarboxylic acid
  -b- Synthesis of the persalt activators and salts thereof The individual steps are explained in more detail below.

The imidocarboxylic acids of the general formula

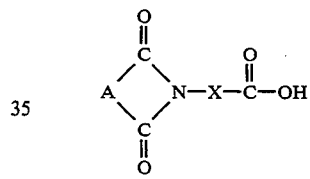

can be prepared in step -a- in a manner which is known per se, as already described in the Patent Application EP-A-349 940, by reaction of anhydrides of the formula

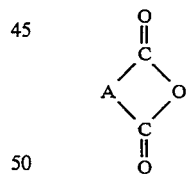

with amino acids of the formula

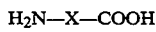

$H_2N$—X—COOH (see Houben-Weyl, Methoden der Organischen Chemie (Methods of Organic Chemistry), XI/2, page 17).

Anhydrides which can be employed are, in particular, succinic anhydride, glutaric anhydride, maleic anhydride, phthalic anhydride, pyromellitic anhydride and alkyl- or alkenylsuccinic anhydrides, and amino acids which can be employed are ω-aminobutyric acid, ω-aminovaleric acid, ω-aminocaproic acid and ω-aminolauric acid.

The imidocarboxylic acids derived from ω-aminobutyric acid, ω-aminocaproic acid and ω-aminolauric acid can also be prepared particularly inexpensively from pyrrolidone, ω-caprolactam or laurolactam. For this, the lactam is introduced into a suitable reaction vessel with the anhydride and with the addition of a catalytic amount of water for 2 to 80 hours, preferably 5 to 25 hours, at a temperature of 100° to 280° C., preferably 120° to 220° C., under an inert gas atmosphere. The increased pressure can be 1 to 50 bar, preferably 2 to 10 bar.

The persalt activators and salts thereof of the formula I which are derived from imidocarboxylic acids can be prepared in step -b- in principle by two different synthesis processes:
the anhydride process
the acid halide process In the one-stage anhydride process, the persalt activators according to the invention are obtained in a one-pot process in which the imidocarboxylic acid is reacted simultaneously with a short-chain carboxylic acid anhydride and a substituted hydroxybenzene derivative. The hydroxybenzene derivatives employed become the leaving groups L of the persalt activators as a result of this reaction.

This reaction can be carried out in the absence of a solvent or, as already described in EP-A-262 895, in an organic solvent. Organic solvents which can be used are, in particular, but not exclusively, high-boiling hydrocarbons, such as, for example, xylene, toluene, octane, decane or dodecane. Nevertheless, the solvent-free reaction is preferred, since the short-chain carboxylic acid anhydrides employed, such as acetic, propionic and butyric anhydride, can also function as solvents. Acetic anhydride is preferred because of its favorable price and its good availability, and for simplicity is mentioned in the following description of the reaction conditions as representative of all the short-chain carboxylic acid anhydrides which can be employed.

Substituted hydroxybenzene derivatives which are employed are o- and p-hydroxybenzenesulfonic acids and salts thereof or o- and p-hydroxybenzenecarboxylic acids and salts thereof, preferably p-hydroxybenzenesulfonic acids and salts thereof and p-hydroxybenzenecarboxylic acids and salts thereof.

To carry out the reaction, a mixture of the substituted hydroxybenzene derivative, acetic anhydride and an imidocarboxylic acid of the formula shown is reacted in a molar ratio of 1:1–5:1–5, preferably 1:1–3:1–3. An alkali metal salt or alkaline earth metal salt of a carboxylic acid, for example sodium acetate, can be added as a catalyst to accelerate the reaction.

It is also possible for the acetoxybenzene derivative first to be prepared in a separate step and for this product then to be transesterified with 1 to 5 mol, preferably 1 to 3 mol, of the imidocarboxylic acid mentioned.

In cases where adequate mixing of the components is not achieved, it may be advantageous to carry out the reaction in a heatable kneader, for example a sigma kneader.

The reaction temperature must be high enough for the acetic acid formed in the course of the reaction to be able to be distilled off. This is in general the case at temperatures of 120°–300° C., preferably at 150°–250° C. The reaction time depends on the nature of the carboxylic acid and of the catalyst.

When the reaction has ended, the reaction mixture is allowed to cool and the excess carboxylic acid and residual amounts of acetoxybenzenesulfonate which have not been transesterified are removed by washing with a solvent. The product purities which can be achieved in this way are good, but can be increased further by frequent washing with a suitable solvent or recrystallization. The solutions obtained by this procedure contain residual amounts of useful substances which can be reused, and they can be reacted again in the subsequent reaction to increase the yield. The overall reaction can therefore also be designed as a continuous reaction by known methods. Preparation methods of this type are described, for example, in EP-A-105 672, EP-A-105 673 and DE-A-3 824 901. Other synthesis processes are described in EP-A-202 698, EP-A-210 674, EP-A-140 251, EP-A-163 224, EP-A-163 225, EP-A-125 641, EP-A-165 480, EP-A-211 045, EP-A-120 591, EP-A-166 571, EP-A-204 116, EP-A-153 222, EP-A-153 223, EP-A-164 786, EP-A-168 876, EP-A-201 222, EP-A-227 194, EP-A-207 445, EP-A-220 656 and EP-A-229 890.

In the two-stage acid halide process, the imidocarboxylic acids are converted into the corresponding acid halides, preferably acid chlorides, in a known manner (Houben-Weyl, Methoden der Organischen Chemie (Methods of Organic Chemistry), Volume E5, p. 593–600). In a second reaction step, the imidocarboxylic acid halides are reacted with the substituted hydroxybenzene derivatives to give the persalt activator according to the invention. In this reaction, the imidocarboxylic acid halides are reacted together with the substituted hydroxybenzene derivatives in a molar ratio of 0.1–2.5:1, preferably 0.5–1.5:1, in an inert high-boiling solvent, for example toluene or xylene, at temperatures between 80° and 200° C., preferably at 100° to 150° C., until no further evolution of gas can be observed. The reaction time is as a rule between 60 and 360 minutes, but can be longer and depends on the reactivity of the acid halide.

After the reaction mixture has been cooled, the solvent is filtered off with suction and the filter cake is washed and/or recrystallized from a suitable solvent.

Analogous reactions are described in the Patent Applications EP-A-98 129, EP-A-148 148, EP-A-164 786 and EP-A-220 826.

The persalt activators and salts thereof of the formula I which are derived from sulfimidocarboxylic acids are prepared by preparation methods analogous to those already outlined, by the following steps:
-c- Synthesis of the sulfimidocarboxylic acid
-d- Synthesis of the persalt activators and salts thereof The steps are explained in more detail below. The sulfimidocarboxylic acids of the formula

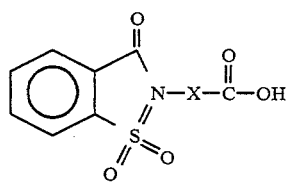

which are called saccharincarboxylic acids, can be prepared in step -c- in a manner which is known per se by reaction of 2-sulfobenzoic anhydride

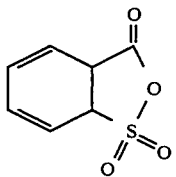

with amino acids of the formula

H$_2$N—X—COOH (U.S. Pat. No. 2,462,835)

The desired sulfimidocarboxylic acids can also be obtained by acid- or base-catalyzed hydrolysis of saccharincarboxylic acid esters (Houben-Weyl, Methoden der Organischen Chemie (Methods of Organic Chemistry), E5, page 223), which are obtained from the reaction of saccharin sodium salt (U.S. Pat. Nos. 1,601,505 and 2,667,503) with halocarboxylic acid esters Hal—X—COOR$^8$, in which Hal is halogen and R$^8$ is C$_1$-C$_5$-alkyl, in dimethylformamide (J. Org. Chem. 21 (1956) 583; and not yet published German Patent Application of Application No. P 4 036 647.2). Saccharincarboxylic acids which differ in their alkyl chain, such as, for example, 3-[1,1,3-trioxo-3H-λ$^6$-benz[a]-isothiazol-2-yl]-propanoic acid, 4-[1,1,3-trioxo-2H-λ$^6$-benz[a]-isothiazol-2-yl]-butanoic acid and 6-[1,1,3-trioxo-3H-λ$^6$-benz[a]-isothiazol-2-yl]-hexanoic acid, are particularly suitable for the preparation of the persalt activators according to the invention.

Two different synthesis routes can likewise be taken to prepare the persalt activators and salts thereof of the formula I which are derived from sulfimidocarboxylic acids in step -d-:
 the anhydride process
 the acid halide process In the one-stage anhydride process, the persalt activators according to the invention are obtained in a one-pot process in which the sulfimidocarboxylic acids are reacted by a process analogous to that described for imidocarboxylic acids.

In the two-stage acid halide process, the sulfimidocarboxylic acids are converted into the corresponding acid halides, preferably acid chlorides, in a known manner. Direct conversion of saccharincarboxylic acid esters into the corresponding saccharincarboxylic acid halides by methods which are known from the literature (Houben-Weyl, Methoden der Organischen Chemie (Methods of Organic Chemistry), E5, page 604) is also possible here.

In a second reaction step, the sulfimidocarboxylic acid halides are then reacted further by a process analogous to that described for imidocarboxylic acids.

In persalt activators having leaving groups of the formula

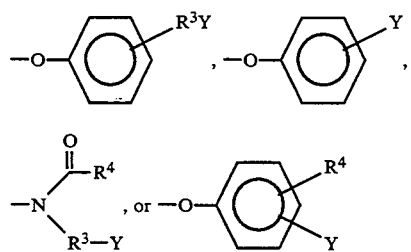

Y can be a substituted ammonium ion —N(R$^7$)$_3$Z or a substituted phosphonium ion —P(R$^7$)$_4$Z. Both in the case of —N(R$^7$)$_3$Z and in the case of —P(R$^7$)$_4$Z, R$^7$ is C$_1$-C$_{30}$-alkyl and Z is a negatively charged counter-ion. In the case of —N(R$^7$)$_3$Z, two of the radicals R$^7$ are preferably C$_1$-C$_4$-alkyl, particularly preferably methyl, and one of the radicals R$^7$ is a longer-chain alkyl group, for example C$_8$-C$_{30}$-alkyl.

In the case of —P(R$^7$)$_4$Z, three of the radicals R$^7$ are preferably C$_1$-C$_4$-alkyl, particularly preferably methyl, and one of the radicals R$^7$ is a longer-chain alkyl group, for example C$_8$-C$_{30}$-alkyl. Both in the case of —N(R$^7$)$_3$Z and in the case of —P(R$^7$)$_4$Z, R$^7$ can be identical or different.

Persalt activators having leaving groups of the formula

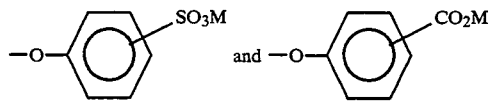

are of particular interest in respect of their preparation, price and water-solubility. A review of the preparation methods published is to be found in the patent applications EP-A-373 743 and JP-A-2 182-795.

The persalt activators according to the invention and salts thereof are solid and virtually odorless, have a low vapor pressure and are of excellent heat stability. They can be used for bleaching, oxidation or disinfection purposes in combination with an inorganic persalt. Inorganic persalts such as sodium perborate monohydrate, sodium perborate tetrahydrate and sodium percarbonate are the preferred inorganic persalt in detergent and bleaching agent formulations for the activators according to the invention.

They are preferably employed as bleaching agents in solid or liquid detergents and cleaning agents, since their bleaching and disinfecting action already becomes fully effective in a wide temperature range below 60° C.

The persalt activators according to the invention or salts thereof are particularly suitable in granulated, extruded, tableted or agglomerated form for incorporation into pulverulent detergents. The persalt activators according to the invention or salts thereof are preferably employed, in basic detergent formulations, in granulated form. Suitable granulating auxiliaries are organic fatty acids, alcohol ethylates, carboxylmethylcellulose or film-forming polymers, such as polyacrylic acids. The persalt activators can be combined with a persalt in granules. In this case, the ratio of persalt to persalt activator is 1:10 to 10:1, preferably 1:3 to 3:1.

Combination with other perborate activators, such as, for example, tetraacetylethylenediamine or sodium nonanonyloxybenzenesulfonate, or organic peroxycarboxylic acids, such as phthalimidoperoxyhexanoic acid or dodecanediperoxydioic acid, in the detergent or cleaning agent is possible.

The detergent formulations can contain, as further additives: anionic, nonionic, cationic or zwitterionic surfactants, inorganic builders, such as zeolite or phyllosilicates, cobuilders, such as polycarboxylates, or organic builders, such as citric acid. Optical brighteners, enzymes and perfumes are also possible.

Very good bleaching results are achieved in the pH range between 8 and 9. The pH of the wash liquor can be changed during the washing process by addition of proton donors (organic or inorganic acids, esters or anhydrides) during the washing process.

The term AS content (AS stands for active substance) in the following examples is to be understood as meaning the content of active substance in the product, which is determined by 2-phase titration by the Epton method (Nature 160, 756 [1947]).

The preparation of the persalt activators according to the invention is illustrated by the following examples:

Example 1

Sodium α-phthalimidoacetoxybenzenesulfonate 500 g of xylene are added to 98.0 g (0.5 mol) of anhydrous sodium phenolsulfonate and 112.0 g (0.5 mol) of α-phthalimidoacetyl chloride and the mixture is kept at 140° C. for 15 hours. After cooling, the reaction mixture is taken up in acetone, the solvent is filtered off with suction over a Büchner funnel and the crystal sludge is washed twice more with 80 ml of acetone each time. After recrystallization from 90% strength ethanol, the resulting product is dried at 40° C. under a water pump vacuum.

Yield: 168 g (88%), melting point > 220° C.
AS content: 93% (Epton titration)

Example 2

Sodium γ-phthalimidobutanoyloxybenzenesulfonate 148.0 g (755 mmol) of anhydrous sodium phenolsulfonate and 190.0 g (755 mmol) of γ-phthalimidobutanoyl chloride are reacted in 200 g of xylene at 140° C. for 4 hours and the mixture is worked up as in Example 1. The crude product is recrystallized from methanol and the white crystalline product is dried at 40° C. under a water pump vacuum.

Yield: 280 g (90%), melting point > 220° C.
AS content: 92% (Epton titration)

Example 3

Sodium ε-phthalimidohexanoyloxybenzenesulfonate 118.0 g (600 mol) of anhydrous sodium benzenesulfonate and 170.0 g (600 mmol) of ε-phthalimidohexanoyl chloride are reacted in 100 g of xylene at 125° C. for 1 hour and the mixture is worked up as described in Example 1. After recrystallization from ethanol, the white product is dried at 40° C. under a water pump vacuum.

$^1$H-NMR (D$_2$O, 100 MHz): δ=1.15–1.83 (m, 6H), 2.5 (t, 2H), 3.6 (t, 2H), 7.0 (m, 2H), 7.5–7.8 (m, 6H).

Yield: 250 g (95%), melting point > 220° C.
AS content: 97% (Epton titration)

Example 4

Sodium ω-phthalimidododecanoyloxybenzenesulfonate 78.5 g (400 mmol) of anhydrous sodium benzenesulfonate and 145.6 g (400 mmol) of ω-phthalimidododecanoyl chloride are reacted in 200 g of xylene at 130°–140° C. for 4 hours and the mixture is worked up as described in Example 1. The product is recrystallized from 90% strength ethanol and then dried at 40° C. under a water pump vacuum.

Yield: 178 g (85%), melting point > 220° C.
AS content = 98% (Epton titration)

Example 5

Sodium ω-(2-dodecylsuccinimido)-acetoxybenzenesulfonate 78.5 g (400 mmol) of anhydrous sodium phenolsulfonate and 137.4 g (400 mmol) of ω-(2-dodecylsuccinimido)-acetyl chloride are reacted in 200 g of xylene at 140° C. for 25 hours and the mixture is worked up as described in Example 1. The product is recrystallized from 90% strength ethanol and then dried at 40° C. under a water pump vacuum.

Yield: 145 g (72%), melting point > 220° C.
AS content = 85% (Epton titration)

Example 6

Sodium ω-trimellitimidohexanoyloxybenzenesulfonate 39.3 g (200 mmol) of anhydrous sodium benzenesulfonate and 64.7 g (200 mmol) of ω-trimellitimidohexanoyl chloride are reacted in 200 g of xylene at 140° C. for 4 hours and the mixture is worked up as described in Example 1. The product is recrystallized from 90% strength ethanol and is then dried at 40° C. under a water pump vacuum.

Yield: 78 g (80%), melting point > 220° C.
AS content = 91% (Epton titration)

Example 7

Sodium ε-phthalimidohexanoyloxybenzenesulfonate 261.0 g (1.0 mol) of ε-phthalimidohexanoic acid, 98.0 g (0.5 mol) of anhydrous sodium phenolsulfonate, 61.0 g (0.6 mol) of acetic anhydride and 2 g of sodium acetate are heated together at 150° C. for 2.5 hours, the reaction mixture already assuming a highly viscous consistency after a short time and becoming difficult to stir. The temperature is then increased slowly to 210° C. and the acetic acid formed is distilled off with the aid of a stream of nitrogen passed over the reaction mixture. The mixture, which is now a thin liquid again, is then kept at 200° C. for a further hour. To dissolve out excess phthalimidohexanoic acid, 400 ml of acetone are added to the still stirrable reaction mixture at about 80° C., while cooling thoroughly, and the mixture is then extracted twice more with 200 ml of acetone each time at 60° C. For further purification, the residue can additionally be washed with ethanol, so that the acetoxybenzenesulfonate formed during the reaction is also dissolved out. As an alternative to the working up described, the hot, thinly liquid reaction melt can also be poured onto a metal sheet to cool, and after solidification can be powdered.

The crude product is then purified with acetone and ethanol.

Yield: 115 g (88%, based on the sodium phenolsulfonate)
AS content: 85% (Epton titration)

Testing of perborate activators based on imidoperoxycarboxylic acids

Example 8

Washing experiments in a Launder-O-Meter

The washing experiments were carried out in a Launder-O-Meter under the following conditions:

| | |
|---|---|
| Water hardness: | 15° dH |
| Washing temperatures: | 20, 40 and 60° C. |
| Washing time: | 15 minutes |
| Detergent: | Mixture of 1.5 g/l of WMP test detergent (WFK) and 0.9 g/l of sodium perborate monohydrate |
| Bleaching test fabric: | Tea on cotton (WFK) Coffee on cotton (WFK) |

-continued

Red wine on cotton (EMPA)

EMPA: Eidgenössiche Materialprüfanstalt, St. Gallen
WFK: Wäschereiforschung Krefeld The perborate activators added were metered in so that in each case 25 mg of active oxygen was present in the form of the corresponding peracid after perhydrolysis had taken place.

The perborate activators employed were:

PAPA: Sodium phthalimidohexanoyloxybenzenesulfonate (according to the invention)

NOBS: Sodium nonanoyloxybenzenesulfonate

When the washing process had ended, the degree of whiteness of the fabric was determined by means of a reflectance photometer. The reflectance values stated are the average over the three bleaching test fabrics.

|  | % Reflectance | | |
| --- | --- | --- | --- |
|  | 20° C. | 40° C. | 60° C. |
| WMP/PB*1 | 50.8 | 50.9 | 52.8 |
| WMP/PB*1/NOBS | 57.0 | 63.0 | 70.3 |
| WMP/PB*1/PAPA | 58.6 | 64.0 | 71.0 |

PB*1: Sodium perborate monohydrate

Example 9

Washing experiments in a Launder-O-Meter

The experiments were carried out analogously to Example 8, with the following changes:

| Detergent | Mixture of 1.5 g/l of phosphate-containing IEC detergent (WFK) and 0.9 g/l of perborate tetrahydrate |
| --- | --- |
| Bleaching test fabric: | Tea on cotton (WFK) Red wine on cotton (EMPA) |

Perborate activators:
A1: Na phthalimidobutanoyloxybenzenesulfonate
A2: Na trimellitimidohexanoyloxybenzenesulfonate
A3: Na phthalimidoacetoyloxybenzenesulfonate
TAED: Tetraacetylethylenediamine (comparison)

|  | % Reflectance | | | |
| --- | --- | --- | --- | --- |
|  | Tea | | Red wine | |
|  | 20° C. | 40° C. | 20° C. | 40° C. |
| A1: | 52.7 | 57.1 | 62.1 | 65.2 |
| A2: | 47.9 | 51.9 | 56.9 | 61.2 |
| A3: | 48.2 | 52.3 | 57.7 | 61.4 |
| TAED | 47.2 | 51.3 | 56.6 | 60.8 |

Example 10

Washing experiments in a Launder-O-Meter

Washing experiments were carried out in the Launder-O-Meter under the following conditions:

| Water hardness: | 5.6° dH |
| --- | --- |
| Washing temperatures: | 25, 40 and 55° C. |
| Washing time: | 15 minutes |
| Detergent: | 2 g/l of Tide ® (including bleaching system) |
| Bleaching system: | 7.5% of sodium perborate monohydrate and 5% of perborate activator (see Example 8) |
| Bleaching test fabric: | Tea on cotton (WFK) Red wine on cotton (WFK) |

-continued

Red wine on cotton (EMPA)

(Tide ® : Detergent, Manufacturer: Procter and Gamble)

|  | % Reflectance*) | | |
| --- | --- | --- | --- |
|  | 25° C. | 40° C. | 55° C. |
| Tide ® /PB*1 | 53.3 | 54.2 | 55.2 |
| Tide ® /PB*1/NOBS | 55.0 | 56.1 | 57.8 |
| Tide ® WMP/PB*1/PAPA | 55.4 | 56.1 | 59.1 |

*) average over the three bleaching test fabrics

Example 11

Multiple washes in a Launder-O-Meter

Washing experiments were carried out in the Launder-O-Meter under the following conditions:

| Water hardness: | 5.6° dH |
| --- | --- |
| Washing temperature: | 40° C. |
| Washing time: | 15 minutes |
| Washing cycles: | 4 |
| Detergent: | 1.5 g/l of Tide ® |
| Persalt: | 0.9 g/l of sodium perborate monohydrate |
| Perborate activators | |
| PAPA: | Sodium phthalimidohexanoyloxybenzenesulfonate (according to the invention) |
| NOBS: | Sodium nonanoyloxybenzenesulfonate (comparison) |
| TAED: | Tetraacetylethylenediamine (comparison) |
| Bleaching test fabric: | Tea on cotton (WFK) Red wine on cotton (EMPA) Remazol Brilliant Red GG ® (textile dyestuff (Hoechst AG)) on cotton |

The perborate activators were metered in so that in each case 3 mg/l of active oxygen was present in the form of the corresponding peracid in the wash liquor after perhydrolysis had taken place.

|  | % Reflectance | |
| --- | --- | --- |
|  | φ Tea/ red wine | Remazol Brilliant Red |
| Tide ® | 47.9 | 26.8 |
| Tide ® /PB*1/TAED | 59.9 | 28.3 |
| Tide ® /PB*1/NOBS | 61.4 | 29.5 |
| Tide ® /PB*1/PAPA | 61.4 | 28.4 |

The results show that the perborate activator PAPA according to the invention shows a good bleaching performance without causing color damage.

Example 12

Washing experiments with a variable pH of the wash liquor

Washing experiments were carried out in a glass beaker under the following conditions:

| Water hardness: | 5.6° dH |
| --- | --- |
| Washing temperature: | 22° C. |
| Washing time: | 15 minutes |
| Detergent: | 1.75 g/l of Tide ® |
| Bleaching system: | 0.1 g/l of perborate activator 0.15 g/l of sodium perborate monohydrate |
| Bleaching test fabric: | Red wine on cotton (EMPA) |
| Starting pH | 10.3 |

-continued of the wash liquor:

5 minutes after the start of the washing process, the pH of the wash liquor was brought to the desired pH using H₂SO₄.

|  | % Reflectance | | |
|---|---|---|---|
|  | pH 10.3 | pH 9 | pH 8 |
| Tide ® | 49.1 | 49.0 | 49.3 |
| Tide ®/PB*1/TAED | 50.6 | 51.9 | 50.7 |
| Tide ®/PB*1/PAPA | 51.2 | 53.0 | 51.9 |

The results show that the bleaching optimum of the perborate activator according to the invention lies in the pH range between 8 and 9.

We claim:

1. A persalt activator or salt thereof which is derived from an imidocarboyxlic acid or sulimidocarboxylic acid of the formula I:

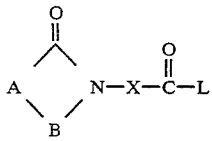

in which A is a group of the formula

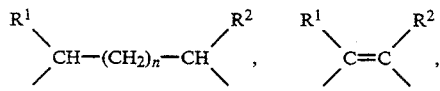

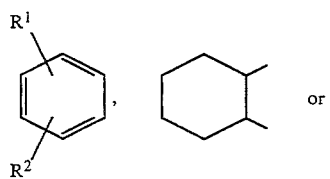

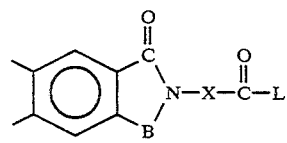

n is the number 0, 1 or 2,
$R^1$ is hydrogen, chlorine, bromine, $C_1-C_{20}$-alkyl, $C_2-C_{20}$-alkenyl, aryl, or alkylaryl,
$R^2$ is hydrogen, chlorine, bromine or a group of the formula —SO₃M, —CO₂M or —OSO₃M,
X is $C_1-C_{19}$-alkylene or arylene
B is a group of the formula C=O or SO₂,
L is a leaving group of the formula

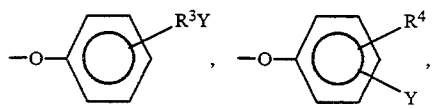

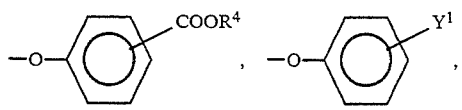

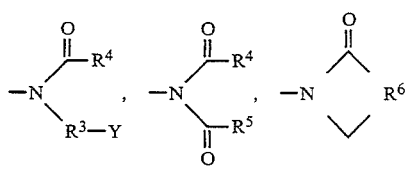

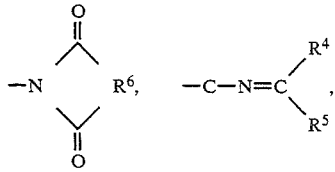

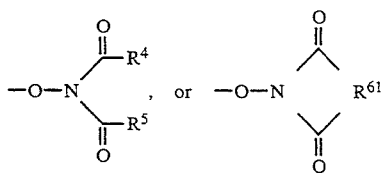

$R^3$ is $C_1-C_{19}$-alkylene,
$R^4$ and $R^5$ are $C_1-C_{20}$-alkyl,
$R^6$ is $C_1-C_{19}$-alkylene or $C_2-C_{20}$-alkenylene,
$R^{61}$ is $C_2-C_{20}$-alkenylene,
Y is hydrogen, chlorine, bromine or a group of the formula —SO₃M, —CO₂M, —OSO₃M, —CONH₂, —N(R⁷)₃Z or —P(R⁷)₄Z,
$Y^1$ is hydrogen or a group of the formula —SO₃M, —CO₂M, —OSO₃M, —CONH₂, —N(R⁷)₃Z or —P(R⁷)₄Z,
$R^7$ is $C_1-C_{30}$-alkyl,
Z is fluoride, chloride, bromide or iodide and
M is hydrogen, an alkali metal or ammonium ion or the equivalent of an alkaline earth metal ion.

2. A compound as claimed in claim 1, in which A is a group of the formula —HC=CH—,

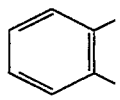

—CH₂—(CH₂)ₙ—CH₂—,

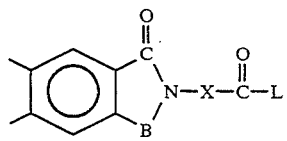

or —CH₂—CHR¹—,
n is the number 0 or 1,
$R^1$ is $C_1-C_{20}$-alkyl or $C_2-C_{20}$-alkenyl,
X is $C_4-C_8$-alkylene,
B is a group of the formula C=O or SO₂,
L is a leaving group of the formula

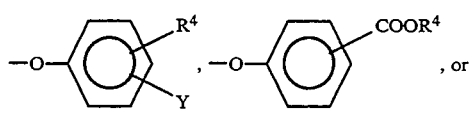, 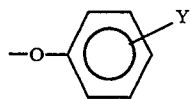

R⁴ is hydrogen or alkyl,
Y is hydrogen or a group of the formula —SO₃M, —CO₂M, —OSO₃M, —CONH₂, —N(R⁷)₃Z or —P(R⁷)₄Z,
R⁷ is C₁-C₄-alkyl,
Z is chloride and
M is hydrogen, an alkali metal or ammonium ion or the equivalent of an alkaline earth metal ion.

3. A compound as claimed in claim 1, in which
A is a group of the formula phenyl or —CH₂—CH-R¹—,
R¹ is C₁-C₂₀-alkyl,
B is a group of the formula C=O or SO₂,
X is C₄-C₈-alkylene,
L is a leaving group of the formula

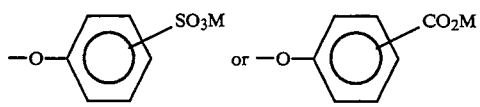

and
M is hydrogen, an alkali metal ion or the equivalent of an alkaline earth metal ion.

4. A compound as claimed in claim 1, in which
R¹ is phenyl or C₁-C₄-alkylphenyl, and
X is phenylene.

5. A compound as claimed in claim 2, in which R⁷ is methyl.

6. A persalt activator or salt thereof comprising a persalt activator or salt thereof derived from an imidocarboxylic acid or sulfimidocarboxylic acid of the formula I:

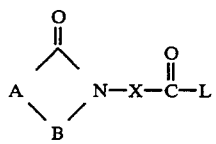 (I)

in which A is a group of the formula

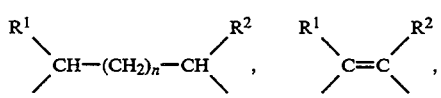

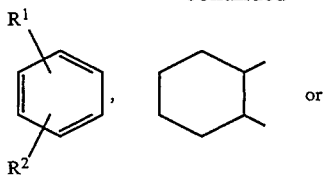

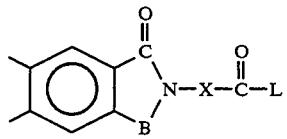

n is the number 0, 1 or 2,
R¹ is hydrogen, chlorine, bromine, C₁-C₂₀-alkyl, C₂-C₂₀-alkenyl, aryl, or alkylaryl,
R² is hydrogen, chlorine, bromine or a group of the formula —SO₃M, —CO₂M or —OSO₃M,
X is C₁-C₁₉-alkylene or arylene
B is a group of the formula C=O or SO₂,
L is a leaving group of the formula

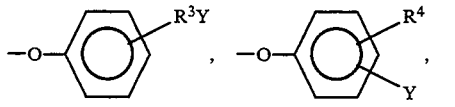

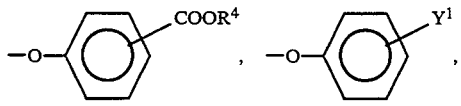

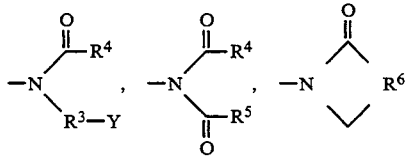

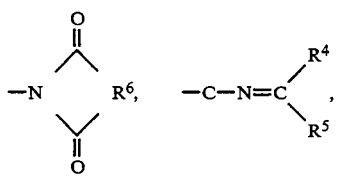

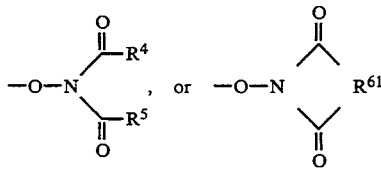

R³ is C₁-C₁₉-alkylene,
R⁴ and R⁵ are C₁-C₂₀-alkyl,
R⁶ is C₁-C₁₉-alkylene or C₂-C₂₀-alkenylene,
R⁶¹ is C₂-C₂₀-alkenylene,
Y is hydrogen, chlorine, bromine or a group of the formula —SO₃N, —CO₂M, —OSO₃M, —CONH₂, —N(R⁷)₃Z or —P(R⁷)₄Z,
Y¹ is hydrogen or a group of the formula —SO₃N, —CO₂M, —OSO₃M, —CONH₂, —N(R⁷)₃Z or —P(R⁷)₄Z,
R⁷ is C₁-C₃₀-alkyl,
Z is fluoride, chloride, bromide or iodide and
M is hydrogen, an alkali metal or ammonium ion or the equivalent of an alkaline earth metal ion.

* * * * *

UNITED STATES PATENT AND TRADEMARK OFFICE
CERTIFICATE OF CORRECTION

PATENT NO. : 5,438,147
DATED : August 1, 1995
INVENTOR(S) : Frank Jaekel et al

It is certified that error appears in the above-indentified patent and that said Letters Patent is hereby corrected as shown below:

On the title page: Item [75] the inventors name should be spelled Wolf-"Dieter Müller".

In item [57] in the abstract, in the second line, the word "sulimidocarboxylic" should read --sulfimidocarboxylic--.

In column 3, line 20 should read --Y is hydrogen, chlorine, bromine or a group of the--.

In column 3, at line 24, the formula "-P(R$^7$)$_4$Z" should read -- -P(R$^7$)$_3$Z --.

In column 4, at line 3, the formula "-P(R$^7$)$_4$Z" should read -- -P(R$^7$)$_3$Z --.

In column 4, at line 68, "ω-caprolactam" should read --ε-caprolactam--.

In column 6, at line 60, the formula should read as follows:

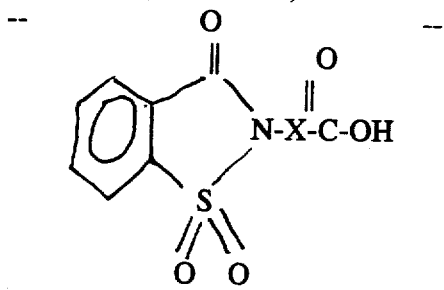

UNITED STATES PATENT AND TRADEMARK OFFICE
CERTIFICATE OF CORRECTION

PATENT NO. : 5,438,147
DATED : August 1, 1995
INVENTOR(S) : Frank Jaekel et al

It is certified that error appears in the above-indentified patent and that said Letters Patent is hereby corrected as shown below:

In column 7, in the first line, the formula should read as follows:

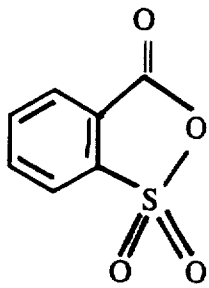

In column 8, at lines 2, 3, 9 and 13, "-P(R$^7$)$_4$Z" should read -- -P(R$^7$)$_3$Z --.

In column 8, at line 56, the word "nonanonyloxybenzene sulfonate" should read --nonanoyloxbenzenesulfonate--.

In claim 1, at line 2 (column 13, at line 22) the word "sulimidocarboxylic" should read --sulfimidocarboxylic--.

UNITED STATES PATENT AND TRADEMARK OFFICE
CERTIFICATE OF CORRECTION

PATENT NO. : 5,438,147

DATED : August 1, 1995

INVENTOR(S) : Frank Jaekel et al

It is certified that error appears in the above-indentified patent and that said Letters Patent is hereby corrected as shown below:

In claim 1, at the definition of L, the second part of the fourth formula should read

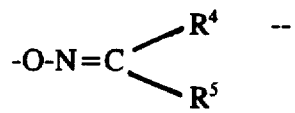

In claim 1, at column 14, lines 36 and 39, the formula "$-P(R^7)_4Z$" should read -- $-P(R^7)_3Z$ --.

In claim 2, at column 15, line 17, the formula "$-P(R^7)_4Z$" should read -- $-P(R^7)_3Z$ --.

In claim 6, column 16, lines 40-45, at the definition of L, the second part of the fourth formula should read

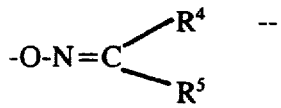

UNITED STATES PATENT AND TRADEMARK OFFICE
CERTIFICATE OF CORRECTION

PATENT NO. : 5,438,147
DATED : August 1, 1995
INVENTOR(S) : Frank Jaekel et al

It is certified that error appears in the above-indentified patent and that said Letters Patent is hereby corrected as shown below:

In claim 6, column 16, at lines 60 and 62, the formula "-SO$_3$N" should read -- -SO$_3$M--.

In claim 6, column 16, at lines 61 and 64 the formula "-P(R$^7$)$_4$Z" should read -- -P(R$^7$)$_3$Z --.

Signed and Sealed this

Fourth Day of February, 1997

Attest:

BRUCE LEHMAN

*Attesting Officer*   *Commissioner of Patents and Trademarks*